United States Patent [19]

Song et al.

[11] Patent Number: 4,814,173

[45] Date of Patent: Mar. 21, 1989

[54] SILICONE ELASTOMER TRANSDERMAL MATRIX SYSTEM

[75] Inventors: Suk-Zu Song, Thousand Oaks, Calif.; Zahra A. Rashidbaigi, Morris Plains, N.J.; Surendra C. Mehta, Randolph, N.J.; Russell U. Nesbitt, Somerville, N.J.; Mahdi B. Fawzi, Flanders, N.J.

[73] Assignee: Warner-Lambert Company, Morris Plains, N.J.

[21] Appl. No.: 93,850

[22] Filed: Sep. 8, 1987

[51] Int. Cl.$^4$ ............................................. A61K 9/70
[52] U.S. Cl. ...................................... 424/444; 424/449
[58] Field of Search ........................ 424/444, 449, 486

[56] References Cited

U.S. PATENT DOCUMENTS

| 3,993,073 | 11/1976 | Zaffaroni | 128/130 |
|---|---|---|---|
| 4,460,371 | 7/1984 | Abber | 604/897 |
| 4,472,372 | 9/1984 | Keith et al. | 424/80 |
| 4,559,054 | 12/1985 | Bruck | 604/892 |
| 4,592,753 | 6/1986 | Panoz | 604/897 |
| 4,601,893 | 6/1986 | Cardinal | 604/890 |
| 4,696,974 | 9/1987 | Sulc et al. | 525/100 |

FOREIGN PATENT DOCUMENTS 0178212 9/1984 European Pat. Off. .

OTHER PUBLICATIONS

U.S. patent application Ser. No. 900,865, filed Aug. 27, 1986, M. Mahjour, et al.

*Primary Examiner*—William R. Dixon, Jr.
*Assistant Examiner*—David M. Brunsman
*Attorney, Agent, or Firm*—Francis J. Tinney

[57] ABSTRACT

A composition for the transmembranal, including transdermal administration of a pharmaceutical preparation comprising medical grade dimethylsiloxane, a catalyst capable of forming an elastomer, a permeation enhancer and a biologically active material, as well as a device for administering the aforementioned compositions and also a method for administering transdermally to a mammal an effective amount of the aforementioned compositions is herein described.

29 Claims, No Drawings

SILICONE ELASTOMER TRANSDERMAL MATRIX SYSTEM

BACKGROUND OF THE INVENTION

Medical grade dimethylsiloxane in combination with a catalyst forms an elastomer capable of delivering therapeutic levels of biologically active materials through mammalian membranes.

Transdermal drug delivery is the diffusion of a therapeutic agent into and through the skin of a mammal. It is an alternative route of administration to oral delivery of various drugs. Advantages of this type of delivery system over oral administration include lack of gastrointestinal problems, reduction of drug metabolism due to initial bypass of the liver, and the ability to continually deliver a systemic amount of a drug over a controlled period of time.

U.S. Pat. No. 3,993,073 to Zaffaroni, A., issued Nov. 23, 1976, discloses a drug delivery device for releasing drug at a controlled rate for a prolonged period of time to produce a local or systemic physiological or pharmacological effect; U.S. Pat. No. 4,460,371 to Abber, H., issued July 17, 1984, discloses a pressure sensitive adhesive; U.S. Pat. No. 4,472,372, to Keith, A. D. and Snipes, W., issued Sept. 18, 1984, discloses a polymeric diffusion matrix containing chlorpheniramine maleate, U.S. Pat. No. 4,559,054 to Bruck, S. D., issued Dec. 17, 1985, discloses a drug release device employing a block copolymer of poly (ether-urethane)/poly (dimethylsiloxane); U.S. Pat. No. 4,592,753 to Panoz, D. E., issued June 3, 1986, discloses a sustained release drug delivery device; U.S. Pat. No. 4,601,893 to Cardinal, J. R., issued July 22, 1986, discloses an improved device for the controlled and prolonged release of at least one active agent to an ambient environment; European patent No. 178212, to Caron, D. and Shroot, B., published Apr. 16, 1986, discloses various pharmaceutical carriers.

The aforementioned disclosures describe various polymeric materials, including medical grade poly (dimethylsiloxane), used as inert carriers for active substances and which in some cases are controllably released from these carriers.

Typically, medical grade poly (dimethylsiloxane) polymers are prepared by vulcanization (polymerization) of medical grade dimethylsiloxane in the presence of stannous octoate catalyst (catalyst M (Dow Corning)). This method of preparation is well-known in the art. See, for example, U.S. Pat No. 4,043,339, and references cited therein.

However, basic drugs such as, for example, chlorpheniramine and diphenhydramine cannot be incorporated into an elastomer of poly (dimethylsiloxane) because the basic drugs interact with the stannous octanoate catalyst used in the curing process and inhibit its vulcanization action.

SUMMARY OF THE INVENTION

Accordingly, we have found that the problem of catalyst poisoning by basic drugs can be resolved by using dibutyl tin dilaurate as a catalyst for the vulcanization reaction.

The present invention relates to a novel composition for the transmembranal, including transdermal, administration of a pharmaceutical preparation comprising medical grade dimethylsiloxane, a catalyst capable of forming an elastomer, such as dibutyl tin dilaurate, a permeation enhancer, and a biologically active material.

A more preferred composition relates to a novel transdermal matrix preparation comprising medical grade dimethylsiloxane, a catalyst such as dibutyl tin dilaurate, a suitable mixture of linoleic acid, triacetin, and propylene glycol, and a biologically active material.

A most preferred composition relates to a novel transdermal matrix preparation comprising medical grade dimethylsiloxane, a catalyst such as dibutyl tin dilaurate, a suitable mixture of linoleic acid, triacetin, and propylene glycol, and a biologically active basic material, such as chlorpheniramine or diphenhydramine.

Chlorpheniramine is an antihistamine known chemically as 2-[p-chloro-α-[2-(dimethylamino)ethyl]benzyl]-pyridine. The compound and its preparation are described in U.S. Pat. Nos. 2,567,245 and 2,676,964 which are hereby incorporated by reference.

Diphenhydramine is an antihistamine known chemically as 2-(diphenylmethoxy)-N,N-dimethylethylamine. The compound and its preparation are described in U.S. Pat. Nos. 2,421,714 and 2,427,878, which are hereby incorporated by reference.

The present invention is also directed to a transdermal device comprising the aforementioned compositions.

The present invention is further directed to a method for administering the aforementioned compositions transdermally to the skin of a mammal.

DETAILED DESCRIPTION OF THE INVENTION

Typically a transdermal drug delivery system consists of a multilayer laminate device comprising an impermeable backing, whose perimeter contains an adhesive, and a matrix system comprising a composition of a drug component admixed in a polymeric gel layered on the inside of the backing. The matrix system is capable of delivering the drug through mammalian skin, including human skin, over a controlled period of time.

The impermeable backing to be used to support the matrix system should be a strong flexible material so that a bandage, foil, or other suitable supportive structure could be fashioned using it. Suitable materials include aluminum, metallized polyester, polyurethane, polyethylene, and the like.

The perimeter of the impermeable backing contains a silicone or acrylic medicinal grade adhesive laminate on the backing for sticking to cutaneous tissue.

The novel matrix system of the present invention contains three components: (1) a carrier component, (2) a permeation enhancement component, and (3) a drug component.

The carrier component contains one or more substantially inert ingredients which function to give the composition physical properties such that it can be effectively administered transmembranally. The carrier component of the present invention comprises about fifty to about ninety-five percent by weight of medical grade poly (dimethylsiloxane) (Silastic ® 382 Medical Grade Elastomer (Dow Corning)) and most preferably about ninety percent by weight of medical grade poly (dimethylsiloxane).

The permeation enhancement component is a substance or a combination of substances which increases the amount of the drug component or components that are transported across biological membranes and into the bloodstream. The permeation enhancement component comprises at least one essential saturated or unsaturated fatty acid, containing from eight to twenty-four carbon atoms, such as, linoleic, or oleic acid comprising about one to about ten percent by weight and most preferably about six percent by weight of linoleic acid. Further the permeation enhancement component contains a solvent or mixture of solvents for the drug component, such as, propylene glycol, glycerol, ethanol, triacetin, triethyl citrate, dimethylisosorbide, ethylene glycol, propoxylated cetyl alcohol, 1-N-dodecylazacycloheptan-2-one (Azone ® (Nelson Research and Development Company)), an alkyl sulfoxide such as, for example, dimethylsulfoxide, and the like comprising about one to about fifteen percent by weight and most preferably about nine percent by weight of propylene glycol and may also comprise about five to about thirty percent by weight and most preferably about fifteen percent by weight of triacetin.

While the above permeation enhancement components are preferred, certain drugs may be transported across biological membranes using only the aforementioned solvents without a saturated or unsaturated fatty acid.

The drug component, such as, for example, chlorpheniramine or diphenhydramine comprises about two to about thirty percent by weight and most preferably about ten percent by weight of chlorpheniramine or diphenhydramine.

The dosage levels to be used in administering the instant compositions containing chlorpheniramine or diphenhydramine are generally consistent with those disclosed in *Remington's Pharmaceutical Sciences*, 17th edition, Mack Publishing Company, Easton, Pa., 1985 at pp. 1127–1128.

While chlorpheniramine or diphenhydramine is used as an example of an antihistamine the present invention also includes other antihistamines as well as other basic drugs that need to be delivered topically and/or systemically. Thus, sedatives, tranquilizers, cognition activators, antihypertensives, analgesics, antiarrhythmics, bronchodilators, cardiotonics, peptides, and the like may be included in the compositions of the present invention.

A base is defined according to the *CRC Handbook of Chemistry and Physics*, ed. Weast, R. C., 67th edition, CRC Press, Inc., Boca Raton, Fla., 1986–1987 at F-69, as "a substance which dissociates on solution in water to produce one or more hydroxyl ions. More generally, however, bases are defined according to other concepts. The Bronsted concept states that a base is any compound which can accept a proton. Thus $NH_3$ is a base since it can accept a proton to form ammonium ions.

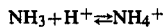

A still more general concept is that of G. N. Lewis which defines a base as anything which has an unshaired pair of electrons. Thus in the reaction

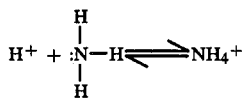

the $NH_3$ is a base because it possesses an unshaired pair of electrons. This latter concept explains many phenomena, such as the effect of certain substances other than hydrogen ions in the changing of the color of indicators. It also explains acids and bases in nonaqueous systems as liquid $NH_3$ and $SO_2$."

Thus, the compositions of the present invention encompasses basic drugs, such as, for example, compounds containing amino groups, various nitrogen heterocycles, and the like.

Illustrative examples of basic drugs falling within the scope of the present invention are the following:

2-[p-[2-Hydroxy-3-(isopropylamino)propoxy]phenyl]acetamide, also known as atenolol, is a β-adrenergic blocker. The compound and its preparation are described in U.S. Pat. Nos. 3,663,607 and 3,836,671 which are hereby incorporated by reference.

1-(Isopropylamino)-3-(1-naphthyloxy)-2-propanol, also known as propranolol, is a cardiac depressant (antiarrhythmic); β-adrenergic blocker. The compound and its preparation are described in U.S. Pat. Nos. 3,337,628 and 3,520,919 which are hereby incorporated by reference.

7,8-Didehydro-4,5α-epoxy-17-methylmorphinan-3,6α-diol, also known as morphine, is a narcotic analgesic. The compound and its preparation are described in Cordell, G. A., *Introduction to Alkaloids*, John Wiley & Sons, New York, N.Y. (1981) pp. 421–428, which is hereby incorporated by reference.

Ethyl 1-methyl-4-phenylisonipecotate, also known as meperidine is a narcotic analgesic. The compound and its preparation is described in U.S. Pat. No. 2,167,351 which is hereby incorporated by reference.

(2R*,6R*,11R*)-1,2,3,4,5,6-Hexahydro-6,11-dimethyl-3-(3-methyl-2-butenyl)-2,6-methano-3-benzazocin-8-ol, also known as pentazocine, is an analgesic. The compound and its preparation is described in Belgium Patent No. 611,000 which is hereby incorporated by reference.

12'-Hydroxy-2'-methyl-5'α-(phenylmethyl) ergotaman-3',6',18-trione, also known as ergotamine, is a vasoconstrictor which may be used in the treatment of migraine. The compound and its preparation is described in Cordell, G. A., *Introduction to Alkaloids*, John Wiley & Sons, New York, N.Y. (1981) pp. 622–636, which is hereby incorporated by reference.

Other conventional adjuncts, such as, colorants, perfumes, stabilizers, and the like can be employed in suitable quantities in th compositions of the present invention.

The novel matrix system of the present invention is useful in the preparation of various devices by which therapeutic agents can be administered transmembranally to mammals. Useful delivery devices include patches, films sprays, swabs, suppositories, creams, gels, and the like with or without supportive backing materials.

The invention is further illustrated but not limited by the following example.

EXAMPLE

Transdermal Patch Containing Chlorpheniramine

Component

Drug: Chlorpheniramine (free base)
Polymer:
50 g Medical grade dimethylsiloxane (Silastic ® 382 Medical Grade Elastomer (Dow Corning))
5 g Dibutyl tin dilaurate (RTVI (Dow Corning))

Permeation Enhancer:
20 percent by weight Linoleic acid
30 percent by weight Propylene glycol
50 percent by weight Triacetin Chlorpheniramine maleate, 15 g, is dissolved in 150 ml of water, to which about 20 ml of ammonium hydroxide is added. The resulting precipitate is extracted with diethyl ether (2×50 ml), washed with water, and dried with anhydrous sodium sulfate. The diethyl ether is evaporated under a stream of nitrogen to give chlorpheniramine free base. The chlorpheniramine free base is dissolved in a mixture of linoleic acid, propylene glycol, and triacetin. The previous mixture is uniformly dispersed in a mixture of medical grade dimethylsiloxane and dibutyl tin dilaurate. The resulting mixture is casted as a membrane on a smooth Teflon surface in a mold and allowed to cure at room temperature for about eighteen hours. The resulting material is applied as a film on adhesive tape.

Diffusion Experiment:

In vitro diffusion experiments were carried out utilizing the matrix composition of the previous example.

Abdominal or back sections from hairless mouse (seven to eight weeks old) skin are mounted on standard Franz ® diffusion cells with the stratum corneum facing the donor compartment. The receiver compartment is filled with warm saline solution (37° C.).

The solution is stirred continuously by a magnetic stirrer at constant speed using a magnetic stirring bar. The transdermal patch containing the matrix composition is applied on the skin. The transport of the drug across the membrane to the receiver solution is monitored by withdrawing the entire volume of the receiver compartment at timed intervals and analyzing for drug by high performance liquid chromatography (HPLC). After each sampling interval the receiver compartment is filled with fresh solvent.

In the experiment, the amount of drug passing through the membrane into the receiver compartment is plotted as a function of time. This transport profile, after initial delay, becomes linear when steady state flux is reached. Extrapolation of this line to zero amount of drug transport, intersects the time axis. This intersect is defined as the lag time.

The results are shown in the following tables.

TABLE I

Effect of Drug Load on Chlorpheniramine Permeation

| Drug Concentration[a] % by Weight | Skin Permeation Enhancer Concentration % by Weight | Flux[b] (mg/10 cm$^2$/day) | Lag Time Hours |
|---|---|---|---|
| 5 | 20 | 44.20 ± 0.22 | 0.11 ± 0.54 |
| 10 | 20 | 50.49 ± 21.49 | 0.44 ± 0.10 |
| 20 | 20 | 89.24 ± 14.32 | 0.46 ± 0.04 |

TABLE II

Effect of Skin Permeation Enhancer on Chlorpheniramine Permeation

| Drug Concentration[a] % by Weight | Skin Permeation Enhancer Concentration % by Weight | Flux[b] (mg/10 cm$^2$/day) | Lag Time Hours |
|---|---|---|---|
| 10 | 0 | 48.42 ± 3.65 | 0.40 ± 0.10 |
| 10 | 11 | 31.84 ± 2.82 | −1.05 ± 1.40[c] |
| 10 | 20 | 50.49 ± 21.49 | 0.44 ± 0.10 |

TABLE II-continued

Effect of Skin Permeation Enhancer on Chlorpheniramine Permeation

| Drug Concentration[a] % by Weight | Skin Permeation Enhancer Concentration % by Weight | Flux[b] (mg/10 cm$^2$/day) | Lag Time Hours |
|---|---|---|---|
| 10 | 30 | 53.05 ± 16.58 | 0.18 ± 0.43 |

[a]Concentrations are expressed as chlorpheniramine maleate.
[b]Flux is the amount of drug passing from a unit area through the barrier over a period of time.
[c]Some of the patches showed "burst" effect (that is, the initial rapid release of drug) rather than lag time.

We claim:

1. A composition for the transmembranal, including transdermal, administration of a pharmaceutical preparation comprising medical grade dimethylsiloxane, a catalyst capable of forming an elastomer wherein said catalyst is dibutyl tin dilaurate, a permeation enhancer, and a biologically active material.

2. A composition of claim 1 where the permeation enhancer consists of a saturated or unsaturated fatty acid containing from eight to twenty-four carbon atoms and a solvent or solvents selected from the group consisting of propylene glycol, glycerol, ethanol, triacetin, triethyl citrate, dimethylisosorbide, ethylene glycol, propoxylated cetyl alcohol, 1-N-dodecylazacycloheptan-2-one and alkyl sulfoxides.

3. A composition of claim 1 where the permeation enhancer is linoleic acid, triacetin, and propylene glycol.

4. A composition of claim 1 where the biologically active material is a sedative.

5. A composition of claim 1 where the biologically active material is a tranquilizer.

6. A composition of claim 1 where the biologically active material is an antihistamine.

7. A composition of claim 1 where the biologically active material is a cognition activator.

8. A composition of claim 1 where the biologically active material is an antihypertensive.

9. A composition of claim 1 where the biologically active material is an analgesic.

10. A composition of claim 1 where the biologically active material is an antiarrhythmic.

11. A composition of claim 1 where the biologically active material is a cardiotonic.

12. A composition of claim 1 where the biologically active material is a bronchodilator.

13. A composition of claim 1 where the biologically active material is a peptide.

14. A composition of claim 1 where the biologically active material is a basic drug.

15. A composition of claim 1 where the biologically active material is diphenhydramine.

16. A composition of claim 1 where the biologically active material is chlorpheniramine.

17. A composition of claim 1 where the biologically active material is atenolol.

18. A composition of claim 1 where the biologically active material is propanolol.

19. A composition of claim 1 where the biologically active material is morphine.

20. A composition of claim 1 where the biologically active material is meperidine.

21. A composition of claim 1 where the biologically active material is pentazocine.

22. A composition of claim 1 where the biologically active material is ergotamine.

23. A transdermal device comprising the composition of claim 1.

24. A transdermal device according to claim 23 which is selected from the group consisting of a patch, film, spray, swab, suppository, cream or gel.

25. A transdermal device comprising the composition of claim 15.

26. A transdermal device comprising the composition of claim 16.

27. A method for administering a biologically active material transdermally to a mammal which comprises applying to the skin of said mammal an effective amount of the composition of claim 1.

28. A method of claim 27 where the biologically active material is diphenhydramine.

29. A method of claim 27 where the biologically active material is chlorpheniramine.

* * * * *